US010054778B2

(12) United States Patent
Frankel

(10) Patent No.: US 10,054,778 B2
(45) Date of Patent: Aug. 21, 2018

(54) ORTHOGONAL CONFOCAL STIMULATED EMISSION MICROSCOPY

(71) Applicant: Robert David Frankel, Rochester, NY (US)

(72) Inventor: Robert David Frankel, Rochester, NY (US)

(*) Notice: Subject to any disclaimer, the term of this patent is extended or adjusted under 35 U.S.C. 154(b) by 0 days.

(21) Appl. No.: 15/466,206

(22) Filed: Mar. 22, 2017

(65) Prior Publication Data

US 2017/0276920 A1  Sep. 28, 2017

Related U.S. Application Data

(60) Provisional application No. 62/311,565, filed on Mar. 22, 2016, provisional application No. 62/347,300, filed on Jun. 8, 2016, provisional application No. 62/427,520, filed on Nov. 29, 2016.

(51) Int. Cl.
| | |
|---|---|
| *G02B 21/00* | (2006.01) |
| *G02B 21/16* | (2006.01) |
| *G01N 21/65* | (2006.01) |
| *G01N 33/483* | (2006.01) |
| *G01N 21/64* | (2006.01) |

(52) U.S. Cl.
CPC ..... *G02B 21/0056* (2013.01); *G01N 21/6458* (2013.01); *G01N 21/65* (2013.01); *G01N 33/4833* (2013.01); *G02B 21/00* (2013.01); *G02B 21/0032* (2013.01); *G02B 21/0048* (2013.01); *G02B 21/16* (2013.01); *G01N 2021/655* (2013.01); *G01N 2021/656* (2013.01); *G01N 2201/067* (2013.01); *G01N 2201/0697* (2013.01)

(58) Field of Classification Search
CPC ............... G02B 21/00; G02B 21/0032; G02B 21/0048; G02B 21/0056; G02B 21/16; G01N 21/6458; G01N 21/65; G01N 33/4833; G01N 2021/655; G01N 2021/656; G01N 2201/067; G01N 2201/0697
USPC ......................................................... 359/385
See application file for complete search history.

(56) References Cited

U.S. PATENT DOCUMENTS

| | | | | |
|---|---|---|---|---|
| 5,046,832 A | * | 9/1991 | Bell | .................. G01M 11/3145 356/73.1 |
| 5,731,588 A | * | 3/1998 | Hell | ...................... G01N 21/63 250/458.1 |
| 9,897,536 B2 | * | 2/2018 | Silien | .................... G01N 21/255 |
| 2003/0179344 A1 | * | 9/2003 | Van de Velde | ......... A61F 9/008 351/200 |
| 2010/0238438 A1 | * | 9/2010 | Frankel | ..................... G01J 3/44 356/318 |
| 2013/0202006 A1 | * | 8/2013 | Rudolph | ............. H01S 3/06741 372/55 |

(Continued)

*Primary Examiner* — William R Alexander
(74) *Attorney, Agent, or Firm* — Tarter Krinsky & Drogin LLP

(57) ABSTRACT

A microscopy system that includes a first laser emitting a first laser pulse along a first beam line, the first laser pulse being a Gaussian pump beam; and a second laser emitting a second laser pulse along a second beam line, the second laser pulse being a probe beam, the Gaussian pump beam and the probe beam being delivered to a sample at right angles to each other allowing the Gaussian pump beam to shrink a focal axial diameter of the second beam line thereby enabling dipole-like backscatter stimulated emission along the second beam line.

22 Claims, 10 Drawing Sheets

(56) References Cited

U.S. PATENT DOCUMENTS

| | | | |
|---|---|---|---|
| 2014/0307249 A1* | 10/2014 | Peremans | G01N 21/636 356/51 |
| 2014/0321772 A1* | 10/2014 | Piche | G02B 21/002 382/284 |
| 2015/0110150 A1* | 4/2015 | Schmidt | G01N 21/1717 374/43 |
| 2016/0103307 A1* | 4/2016 | Frankel | G02B 21/0076 600/317 |
| 2017/0219489 A1* | 8/2017 | Cheshnovsky | G02B 27/1013 |
| 2017/0278694 A1* | 9/2017 | Chuang | H01J 61/025 |

\* cited by examiner

FIGURE 1A
a) Energy levels 1,1-Photon
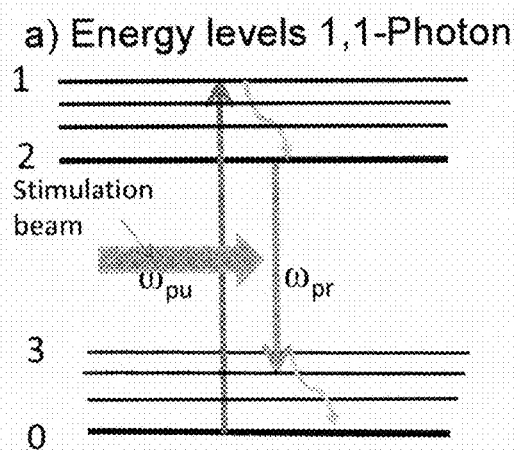
FIGURE 1B
b) Energy levels 2,1-Photon
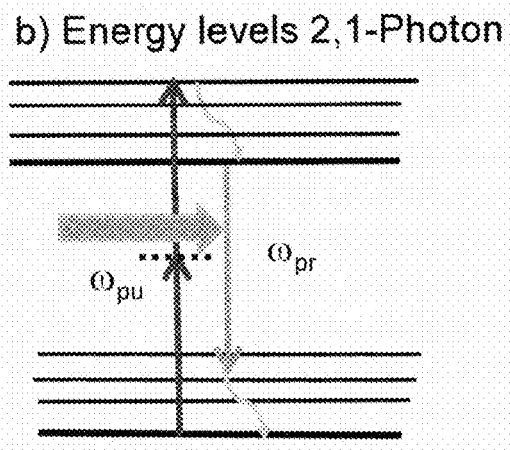
c) Energy levels 2,2-Photon
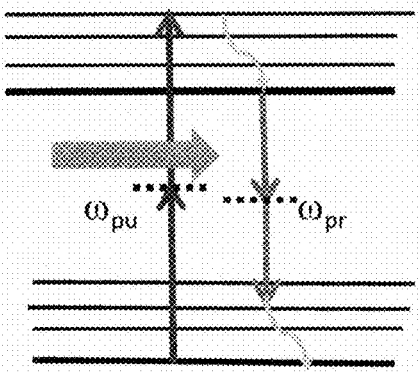
FIGURE 1C
d) Energy levels 3,3-Photon
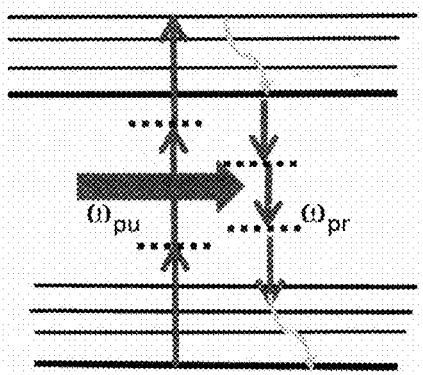
FIGURE 1D

| Molecule | 1 Photon | | 2 Photon | | 3 Photon | | 4 Photon | |
| --- | --- | --- | --- | --- | --- | --- | --- | --- |
| | Pump | Probe | Pump | Probe | Pump | Probe | Pump | Probe |
| DNA | 260nm | 320nm | 520nm | 640nm | 780nm | 960nm | 1040nm | 1240nm |
| Protein | 280nm | 340nm | 540 nm | 680nm | 840nm | 1020nm | 1120nm | 1360nm |
| NADH | 340nm | 455 nm | 680nm | 910nm | 1020nm | 1365nm | 1360nm | 1820nm |
| FAD | 450 nm | 520 nm | 900nm | 1040nm | 1350nm | 1560nm | 1800nm | 2080nm |

FIGURE 5

ORTHOGONAL CONFOCAL STIMULATED EMISSION MICROSCOPY

CLAIM OF PRIORITY

This application claims the benefit of U.S. Provisional Application No. 62/311,565, filed on Mar. 22, 2016, U.S. Provisional Application No. 62/347,300, filed on Jun. 8, 2016, and U.S. Provisional Application No. 62/427,520, filed on Nov. 29, 2016, all of which are hereby incorporated by reference in their entireties.

CO-PENDING APPLICATION

The following co-pending patent application, U.S. patent application Ser. No. 15/466,172, entitled "Depth And Speed Enhanced Orthogonal Beam Stimulated Fluorescent And Stimulated Raman Emission For In-Vivo Imaging" is being filed concurrently herewith and is hereby incorporated by reference in its entirety.

BACKGROUND

This disclosed technology relates to stimulated emission fluorescence and stimulated Raman microscopy and more particularly to in-vivo and in tissue culture stimulated emission.

There is interest in providing deep imaging for use in research, neuroscience, endoscopy, dermatology and intra-surgical definition of clear margins during removal of malignant tissues. For example, Optical Coherence Tomography (OCT) can obtain images up to 1 mm depth in tissue.

In addition there is interest in imaging low concentrations of molecules that do not fluorescence or have week fluorescence such as small drug molecules, metabolic cofactors, and messengers such as ATP and neurotransmitters.

Multi-Photon Excitation (MPE) imaging can enhance the depth of penetration by using infrared photons for excitation where tissue absorption is low. MPE uses two or more photons to excite emission as shown in FIG. 1b. In MPE, the two or more photons can be simultaneously absorbed by one molecule, through the population of one, or more, very short lived virtual states.

MPE excitation has also been used in Fluorescence Lifetime Microscopy (FLIM), for example, to measure the fluorescent lifetimes of bound and free state metabolic cofactor NADH. Fluorescent lifetimes are of importance when determining a metabolic state of cells, in accessing tissue health and differentiating normal from malignant cells. MPE, however, is relatively slow because the fluorescent yield of free NADH is low, has a short excited state lifetime and needs photon counting to create a decay curve.

Standard fluorescence is an incoherent spontaneous emission process where emission of one or multiple photons causes fluorescent emission. In standard fluorescence, the incoherent spontaneous emission can be red shifted from the excitation and can be considered a dark field imaging technique. The measurement process for standard fluorescence is limited to background fluorescence and electrical noise.

Stimulated fluorescent emission (STEM) imaging is a combination of incoherent and coherent processes. (the energy level diagram is shown in FIG. 1a) that uses two photons—a pump and a probe. The pump excites an electron into excited state $S1$ from ground state $S0$. A several hundred femtosecond delay, or more, is allowed for the decay of an excited state vibrational level into the lowest excitation level in the excited state manifold $S2$ via a Kasha decay process. Then a probe (or stimulated emission) beam causes the stimulated emission of a photon and the de-excitation of the electron to $S3$, which then rapidly decays via a Kasha decay process back to $S0$. The signal measured is a gain in the probe beam or loss in the pump beam. STEM techniques have been used to image molecules that absorb strongly, but do not fluoresce efficiently such as oxy-hemoglobin, deoxy-hemoglobin, melanin, cytochromes and certain drugs.

STEM is a bright field technique where a signal is added to the forward propagating probe beam. The gain in the beam is $10^{-4}$-$10^{-7}$ (depending on concentration). Therefore, sophisticated electronic signal processing lock-in techniques are usually required to detect a small probe beam change. STEM imaging also uses moderate to high concentrations of molecules to image tissue at moderate to high speed. Unlike fluorescence imaging where emission occurs in any direction, the emission in STEM occurs in the forward direction. Therefore multiple scattering events are required to collect the signal at the tissue surface. STEM is best used for weakly absorbing and scattering tissues but the depth of imaging is limited and requires collection at an angle outside of the imaging aperture, eliminating the ability to do confocal imaging and degrading signal to noise ratio by collecting photons that scatter prior to reaching focus.

Multi-Photon Stimulated Emission Microscopy (MP-STEM) can be used to enhance the depth of penetration and reduce the scattering and absorption of stimulated emission photons in STEM microscopy. MP-STEM uses multiple photons for both excitation and to stimulate emission from weakly fluorescent molecules. The process of MP-STEM can reduce the focal spot size of the emitting region. When using 3 photons or more, the focal spot is reduced in size enough to cause the stimulated emission spot to be small enough to cause dipole-like backscatter emission. This occurs when the axial dimension of the emitting region shrinks to less than 50% of the Stimulated emission wavelength. Dipole backscatter enables enhancement of the detected Signal to Noise Ratio (SNR) because in the backscattered direction the noise is due to the Refractive Index (RI) gradient and MIE scattering from the emission region focus in confocal microscope geometry. This is less than the forward scattered noise normally detected in STEM microscopy, or multiple backscatter STEM detection.

Raman stimulated emission microscope (Ra-STEM) works the same way as single photon fluorescence STEM. Here the excitation occurs in vibrational rather than electronic levels. The mechanism of Ra-STEM is similar to fluorescence STEM, except the excited state produced by the pump is a virtual level of very short lifetime, thus the pump and probe should arrive simultaneously at the sample. Again unless the focal spot is less than ½ the probe wavelength almost all of the stimulated light is scattered in the forward direction.

Thus there are deficiencies in the use of MP-STEM and Raman-STEM
1. The focal spot shrinkage in 1, 2 and 3 photon MP-STEM and 1 photon Raman-STEM is not small enough to provide optimal dipole backscatter.
2. Overlap of converging pump and probe beams may result in stimulated emission outside of the focal region from focal spot enlargement due to refractive index gradients, or relatively high power near focus.
3. Optimal focal spot reduction uses high Numerical Aperture (NA) imaging. This, typically, does not enable large standoff distances that can be desirable for in-vivo imaging or imaging in culture medium.

SUMMARY

The disclosed technology relates to single and multi-photon stimulated emission microscopy used to increase depth of focus in in-vivo stimulated fluorescence imaging and Stimulated Raman Scattering, to reduce photo-bleaching of examined tissues, and to provide focal spot reduction enabling dipole like backscatter and provide enhanced signal to noise ratio (SNR) for low concentrations of molecules under study. The disclosed technology can be applied to many applications including vibrational transitions; to image the metabolism of cells in-vivo, cerebral metabolism, as well as, stimulated emission from lipids, proteins, and nucleic acids and to provide label-less stimulated emission contrast imaging and fluorescence lifetime data from molecules in tissue with multiple component lifetimes.

In one implementation, a microscopy system can comprise: a first laser emitting a first laser pulse along a first beam line, the first laser pulse being a Gaussian pump beam; and a second laser emitting a second laser pulse along a second beam line, the second laser pulse being a probe beam, the Gaussian pump beam and the probe beam being delivered to a sample at right angles to each other allowing the Gaussian pump beam to shrink a focal axial diameter of the second beam line thereby enabling dipole-like backscatter stimulated emission along the second beam line. In some implementations, the Gaussian pump beam and the probe beam can remain confocal and can be phased to scan across the sample.

In some implementations, the microscopy system can further comprise: a first objective having a numerical aperture greater than 1, the first objective being positioned along the first beam line; and a second objective having a numerical aperture less than the first objective, the second objective being positioned along the second beam line, wherein the second objective has an axial stimulated emission focal region half width diameter less than 50% of a wavelength of a stimulated emission photon.

In some implementations, the Gaussian pump beam can be focused to a spot in a sample. In some implementations, the second beamline can collect the dipole-like backscattered stimulated emission and can focus the dipole-like backscattered stimulated emission on a confocal aperture. In some implementations, the probe beam can include a Gaussian spot at focus.

In some implementations, the microscopy system can further comprise: at least one time delay component along the second beam line for delaying the probe beam, the at least one time delay component delaying the probe beam by 0.001 ps to 5 ns relative to the pump beam.

In some implementations, the microscopy system can further comprise: a galvanometer scanning system along the first beam line that confocally scans the Gaussian pump beam locked to a galvanometer scanning system along the second beam line that scans the probe beam which fills in a two dimensional image in a detector located along the second beam line.

In some implementations, the microscopy system can enable reduction of an axial half width dimension of a stimulated emission focal spot to less than 50% of a wavelength of a stimulated emission photon. In some implementations, the microscopy system can further comprise: an acousto-optic modulator for modulating the Gaussian pump beam on and off.

In another implementation, a microscopy method can comprise the steps of: emitting a first laser pulse along a first beam line, the first laser pulse being a Gaussian pump beam; and emitting a second laser pulse along a second beam line, the second laser pulse being a probe beam, delivering the Gaussian pump beam and the probe beam to a sample at right angles to each other allowing the Gaussian pump beam to shrink a focal axial stimulated emission region diameter of the second beam line thereby enabling dipole-like backscatter stimulated emission along the second beam line.

In some implementations, the Gaussian pump beam and the probe beam can remain confocal and can be phased to scan across the sample. In some implementations, the Gaussian pump beam can be focused to a spot in a sample. In some implementations, the probe beam can include a Gaussian spot at focus.

In some implementations, a first objective can be positioned along the first beam line and have a numerical aperture greater than 1, and a second objective can be positioned along the second beam line and have a numerical aperture less than the first objective, the second objective producing an axial focal spot diameter less than 50% of a wavelength of a stimulated emission photon. If MP-STEM is used the NA of the beamline 1 objective may be 0.8-0.9 because the diameter of the pump excitation region is a made smaller by the requirement of two photons exciting target molecules. In some implementations, the second beamline can collect the dipole-like backscattered stimulated emission and focus the dipole-like backscattered stimulated emission on a confocal aperture array. In some implementations, the microscopy can further comprise the step of: delaying the probe beam by 0.001 ps to 5 ns relative to the pump beam.

In some implementations, the microscopy can further comprise the step of: scanning the Gaussian pump beam along with the first beam line to fill in a two dimensional image in a detector located along the second beam line. In some implementations, the microscopy can further comprise the step of: scanning the probe beam along the second beam to fill in focal spots of the Gaussian pump beam.

In some implementations, the microscopy system can enable reduction of an axial stimulated emission region dimension of a stimulated emission focal spot to less than 50% of a wavelength of a stimulated emission photon. In some implementations, the microscopy can further comprise the step of: modulating the Gaussian pump beam on and off.

In one implementation, a microscopy system can comprise: a first laser emitting a first laser pulse, the first laser pulse being a pump beam; a second laser emitting a second laser pulse, the second laser pulse being a probe beam; time delay components for delaying the probe beam, wherein the time delay components delay the probe beam by 0.001 ps to 5 ns relative to the pump beam; two separate optical beam lines with appropriate delays to deliver the beams to the sample at right angles to each other. One beamline, called Beamline 1 can produce a Gaussian beam that may be focused to a spot in the sample. There can be a galvanometer scanning system that scans the beam to fill in a two dimensional image in the detector in the second beam line. The second beam line, called beamline 2, can produce a probe beam that includes a Gaussian spot at focus. The second beamline probe beam can produce stimulated emission. There can be galvanometer scanning systems in the second beam line that fills in the focal spots. Beamlines 1 and 2 can remain confocal and be spatially locked to scan across the tissue together. The second beamline can collect the direct dipole backscattered stimulated emission light and focus this light on a confocal aperture in front of a differential or phase sensitive imager array designed for detecting signals with high dynamic range. The beamline 1 and beamline 2, in most cases, are orthogonal to each other. This microscope configuration is called Orthogonal Confocal Stimulated Emission Microscopy (OR-STEM).

The Point Spread Function (PSF) of a single or multiphoton stimulated emission microscope is the product of the pump PSF to the power of the number of photons used to excite the transition, multiplied by the probe PSF multiplied by the power of the number of probe photons used to stimulate the transition. In the multiphoton OR-STEM disclosed here the Beamline 2 focal spot axial dimension perpendicular to the pump Beamline 1, and along the plane of focus of Beamline 1 makes the axial dimension of the probe stimulated emission region small enough to enable stimulated emission dipole backscatter. This is also true for single photon STEM, if the NA of the pump beam is made greater than NA=1.0 and the pump NA=0.6-0.9.

The orthogonal combination of High NA pump beam and smaller NA probe beam can produce an axial focal spot stimulated emission regions diameter less than 50% of the wavelength of the stimulated emission photon; wherein the reduced focal spot size enables the stimulated emission having dipole-like backscatter. This backscatter can be collected by a detector for enabling imaging of the dipole-like backscatter. In some implementations, at least two photons can be used for both excitation and stimulation of a targeted molecule. In some implementations, the stimulated emission of the targeted molecule can be red shifted by enabling the excited state fluorescent electronic transition to the ground state vibrational levels to occur via a multiphoton stimulated transition of the molecule; where the sum of the energies of the multiple stimulated emission probe photons is resonantly about equal to the energy of the fluorescent transition In some implementations, the stimulated emission of the targeted molecule can be used to measure a metabolic state of cells deep within tissues via a measurement of a concentration of metabolic cofactors NADH and NADPH, in both free and bound states. In some implementations, the multiphoton stimulated emission occurs in proteins or nucleic acids and is used as image tissues without stain. In some implementations the stimulated emission is used to measure the concentrations of melanin and its derivatives. In some implementations, single photon Raman STEM can be used to image C=H bonds in proteins, DNA and lipids, or isotope or chemical group labeled drugs, glucose or proteins.

In some implementations, the time delay components can include an optical switch in the probe beam line to switch the probe beam between at least two delay lines. In some implementations, the optical switch can allow at least two different temporal delays between the pump beam and the probe beam so that molecular fluorescence lifetime can be calculated. In some implementations, the optical switch can be a Mach-Zehnder interferometer.

In some implementations, the combined laser pulses can be used to excite an electron into an electronic excited state that emits stimulated emission from its lowest energy excited state level.

In some implementations, the microscopy system can further comprise: an acousto-optic modulator for modulating the pump beam on and off. In some implementations, the collection apparatus can generate an imaging signal corresponding to a gain in intensity of the probe beam computed as the difference between the combined laser pulse with the pump beam on and the combined laser pulse with the pump beam off.

In another implementation, a microscopy method can comprise the steps of: emitting a first laser pulse, the first laser pulse being a pump beam; emitting a second laser pulse, the second laser pulse being a probe beam; delaying the probe beam, wherein the time delay components delay the probe beam by 0.001 ps to 5 ns relative to the pump beam; combining the pump beam and the delayed probe beam into a combined laser pulse, the combined laser pulse having a reduced focal spot size; delivering the combined laser pulse to a focal spot in a focal plane, wherein the reduced focal spot size of the combined laser pulse initiates a stimulated emission of a targeted molecule, the stimulated emission having dipole-like backscatter; and enabling imaging of the dipole-like backscatter.

In some implementations, the microscopy method can further comprise the step of: modulating the pump beam on and off. In some implementations, the collection apparatus can generate an imaging signal corresponding to a gain in intensity of the probe beam computed as the difference between the combined laser pulse with the pump beam on and the combined laser pulse with the pump beam off.

Advantages of the disclosed technology include an enhancement of backscatter for 1, 2 and 3 photon STEM microscopy configurations, increasing the SNR of the collected signal via enhanced dipole backscatter, reduced photo damage by having orthogonal beamlines for the pump and probe beams.

BRIEF DESCRIPTION OF THE DRAWINGS

FIG. 1*a* is a graphical depiction of an energy diagram of 1 photon STEM;

FIG. 1*b* is a graphical depiction of an energy diagram of 2 photon excitation and 1 photon stimulated emission STEM;

FIG. 1*c* is a graphical depiction of an energy diagram of MP-STEM (2 pse);

FIG. 1*d* is a graphical depiction of an energy diagram of 3 photon MP-STEM (3 pse);

FIG. 5 is a table showing 1 photon, 2 photon, 3 photon and 4 photon pump excitation and probe stimulated emission wavelengths for biological molecules;

DETAILED DESCRIPTION

The disclosed technology is related to systems and methods that enable deep tissue imaging through the use of 1-4 pump photons to excite a molecule of a sample tissue, through zero or more virtual excited states. In addition, stimulated emission photon beams with photons of 100%, 50%, 33% or 25% of the energy difference of the lowest level excited state and an excited level in the ground state manifold can be used to stimulate the emission of 1, 2, 3, or 4 photons that can be added to a stimulated emission beam. This emission can occur as the excited state electron is moved from the excited state to the ground state manifold through zero or more virtual energy levels via a single or multi-photon stimulated emission process. In Stimulated Raman, the excited state is a virtual state, unless resonance Raman excitation is used.

The disclosed technology uses single or multi-photon excitation with a Gaussian beam to shrink the focal axial length of the orthogonal stimulated emission optical beam-line to subwavelength probe photon (stimulated emission photon) dimensions. This shrinking of the focal axial diameter enables dipole-like backscatter stimulated emission and direct ballistic photon backscatter imaging from deep within tissues.

The disclosed technology can be used to measure the concentrations of both fluorescent and poorly-fluorescent states of the enzyme cofactors NADH and FAD, map the metabolic state of a tissue under study and map many chromophores that are not fluorescent such as drugs, nucleic acids and proteins.

The disclosed technology can also enable label-free in-vivo stimulated auto-fluorescent, or Stimulated Raman, imaging for medical research, endoscopy, dermatology and define clear margins in cancer surgery using low and high quantum efficiency emitters. In one implementation, Multi-Photon Stimulated Fluorescent (MP-STEM) can enable enhanced depth of penetration of imaging of drugs, metabolic metabolites and direct fluorescent imaging of DNA, RNA and protein fluorescence in living tissue. That is, the MP-STEM process enables collection of direct backscattered photons into the imaging apertures of a confocal array from a dipole-like emission created using 1, 2, 3 and 4 photon stimulated emission processes. MP-STEM enables deep tissue imaging of weak, as well as, strong, fluorescent molecules emitted in both the visible and UV regions of a spectrum. In some implementations, MP-STEM can be a multiphoton process for both excitation and generation of stimulated emissions, which in turn, red shifts stimulated emission photons for enhanced imaging.

Figure 9:
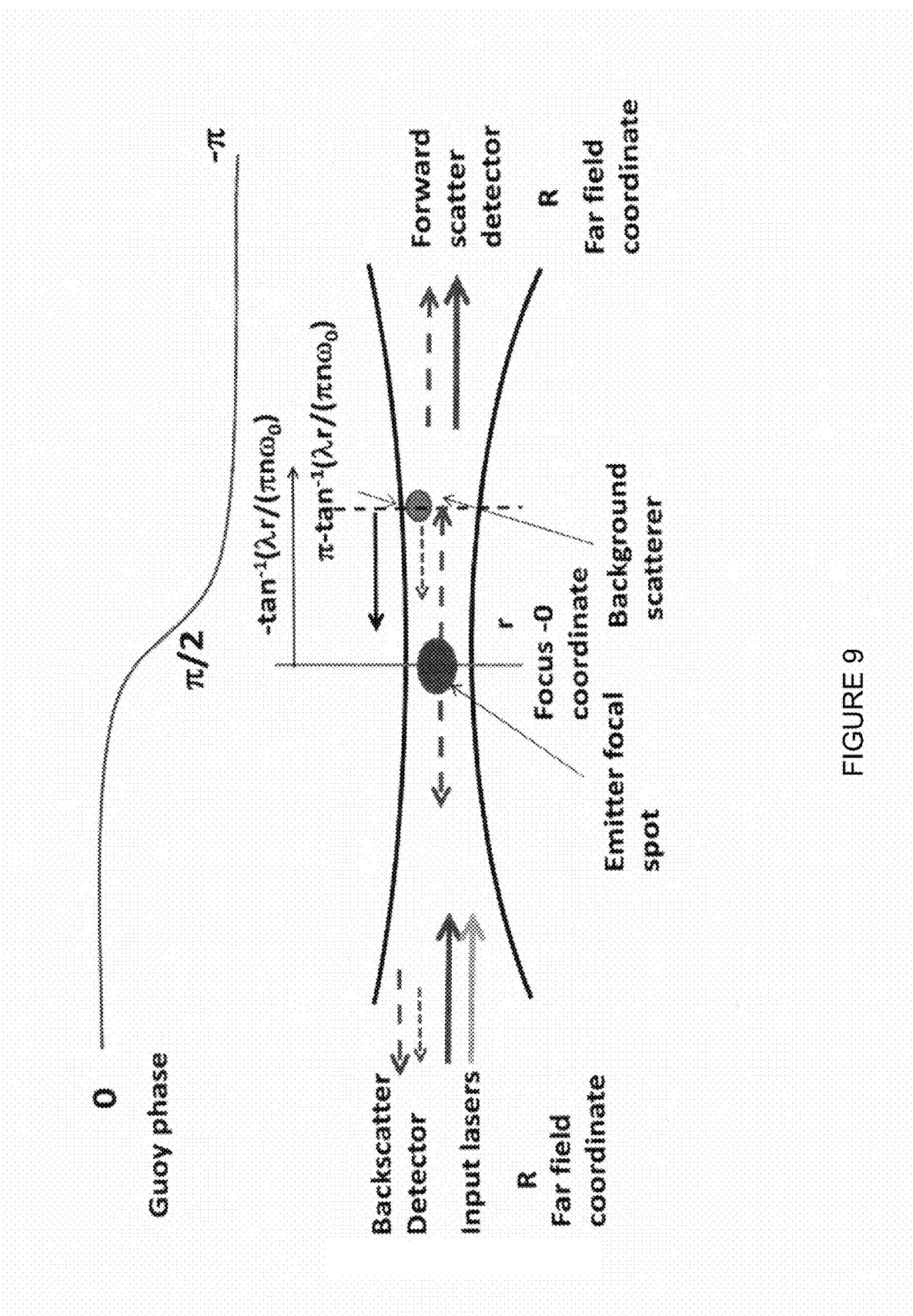
FIG. 9 is an illustration of a direction of the stimulated emission in normal sized focal spots and OC-STEM spots reduced to <50% of the probe wavelength in the axial direction and is an illustration of a Position of Index of Refraction backscatter relative to focus and the relationship to Gouy phase.

A single fluorophore emits stimulated emission into the backward illumination and forward propagating modes in to the stimulating mode with equal probability. This occurs, in part because the fluorophore is small relative to the optical wavelengths of the stimulating photon. However, it is known that as stimulated emission gain length of a volume of emitters increases, dipole backscatter quickly decreases. Although in a microscope the gain in the stimulated field can be small, if the focal spot is small, as the probe beam propagates along the forward direction through the focal spot the stimulated emission photons add in phase to the stimulating beam, increasing the forward traveling coherent traveling field. The stimulated emission in the back propagation direction adds out of phase as the incident stimulating beam propagates forward. Thus as the gain medium length increases, the backscattered stimulated emission photons from axially spatially separate fluorophores destructively interfere. The backscatter stimulated field quickly decreases over sub-wavelength dimensions. This is much shorter than may a confocal microscope axial focal spot. It is desirable to maximize the direct backscattered signal. The background noise characteristics in STEM imaging of dipole emitters are different in the forward and backscattered directions. In the forward direction the background noise can be primarily from photons in the excitation probe beam and can be more intense than accompanying probe stimulated emission. This is also the case for collection of multiply scattered epi collected signals. For backward propagating dipole emission in confocal microscope geometry, the background noise comprises backscattered probe photons from within the focal volume of the microscope, and multiplies scattered photons that enter into the confocal aperture system. The direction and sources of collected signal and noise photons is shown in FIG. 9.

Most backscattered photons within the microscope focal spot come from refractive index (RI) gradients in the focal volume. This noise can be about $5 \times 10^{-4}$ of the incident beam, at the interface of cytoplasm and cell nuclei. Thus backscatter noise can be less than forward noise, reducing the incident flux for STEM imaging. In addition, by reducing the noise, lock-in, differential or phase based data collection techniques may not be required.

Figure 8:
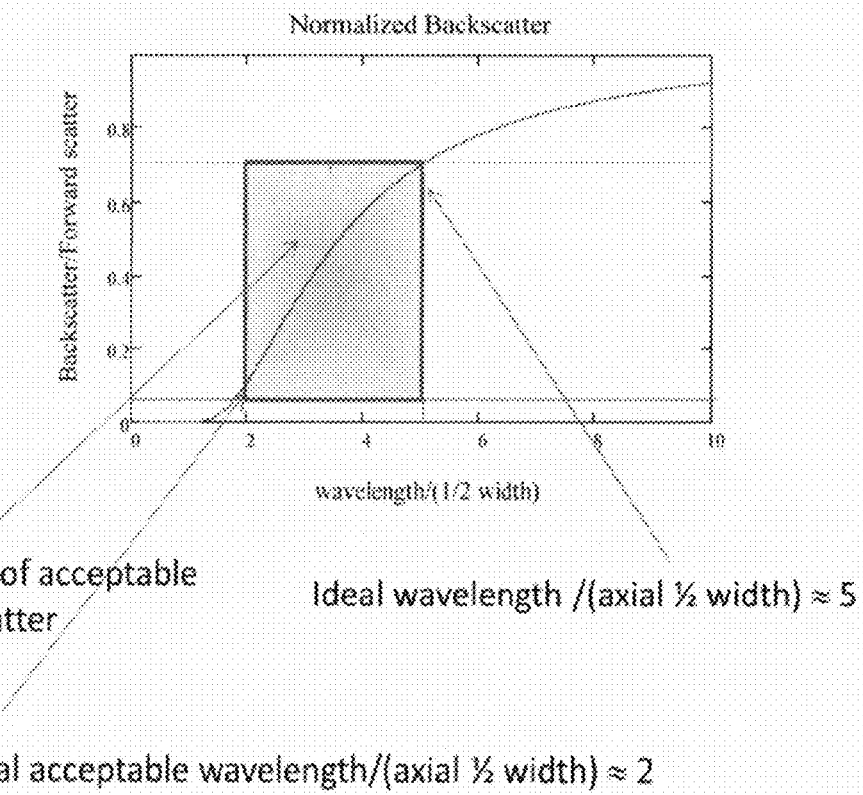
FIG. 8 is a graphical depiction of a ratio of back scattered to forward scattered stimulated emission as a function ratio of emission wavelength to emission axial ½ widths.

FIG. 8 plots the ratio of back scattered to forward scattered stimulated emission as a function the ratio of emission wavelength/(emission axial focal spot ½ width). When the axial probe length is less than ½ of the wavelength, the backscatter is adequate to use for imaging applications. The optimal axial length is about ⅓ of the probe wavelength for a volume of emitters. Smaller focal spots result in much smaller emission, unless emitting molecules are concentrated in a smaller area than the emitting spot.

In co-pending U.S. patent application Ser. No. 14/881,701, hereby incorporated by reference, 2 photon stimulated emission in conjunction with a third beam—the donut beam was used to reduce the focal spot to dimensions of the axial focal spot to less than 50% of the probe wavelength to cause stimulated emission in the backscattered dimension.

In co-pending U.S. patent application Ser. No. 14/949,612, hereby incorporated by reference 2-4 photon are used both for pumping the excited state and stimulated emission to reduce the focal spot size to dimensions of the axial focal spot to less than 50% of the probe wavelength to cause stimulated emission in the backscattered dimension.

This disclosure includes the following:

1. A method and system using 2 microscope objectives at right angles. One beam path is used to create a Gaussian beam to enable a multi-photon pump illumination at the focal region of the pump high NA microscope objective. The second beam path is used for confocal delivery of a stimulated emission photon beam to the microscope focus in the form of a Gaussian beam. The stimulated emission beam can be used to enable 1-4 photon stimulated emission. The second beamline is also used to acquire the dipole-like stimulated emission backscatter though an array of confocal apertures in front of a phase detection detecting system or a photodiode. When 2 or more photons are used for stimulated emission to cause stimulated fluorescent emission that is red shifted compared to the standard blue or UV fluorescent emission, this is called Multi-Photon Stimulated Emission (MP-STEM) imaging.
2. The techniques described above can be used to image 1 photon or multiphoton direct backscattered stimulated emission from proteins, nucleic acids, drugs and molecular cofactors in vivo without the use of stains.

The energetics of pump and a probe beams used in stimulated fluorescent emission (STEM) imaging are shown in FIG. 1a. The pump excites an electron to state S1 from S0.

The excited electron decays to the lowest energy excited state S2 via a rapid Kasha decay process decay process. Then a probe (or stimulated emission) beam causes the emission of a photon and the de-excitation of the electron to S3, which then rapidly decay via a Kasha decay process back to S0.

Multiphoton excitation, as shown in FIG. 1b, is widely used in fluorescent microscopy to enhance the depth of penetration of excitation light and to reduce the photobleaching of molecules positioned out of focus.

Multiphoton stimulated emission takes advantage of the fact that the Einstein absorption and stimulated emission coefficients are similar. Multiphoton stimulated emission red shifts the blue and UV fluorescent emission into the green, red or near IR. Two photon stimulated emission (2 pse) energy levels are shown in FIG. 1c. FIG. 1d shows the energetics of three photon excitation and three photon stimulated emission (3 pse). Using 2 or more photons for both excitation and stimulation is called Multiphoton Stimulated Emission (MP-STEM) microscopy.

MP-STEM is distinct from all previous types of multiphoton microscopy. Each excited electron transition to the ground state vibrational manifold adds two stimulated emission photons to the probe beam used to measure gain in 2 pse processes. Each photon has about ½ the energy of the single photon transition. Three photons are added to the probe beam in a 3 pse process for each molecular stimulated emission. Each photon in 3 pse has about ⅓ the energy of the single photon transition.

Use of MP-STEM microscopy can enable direct in-vivo tissue imaging of the UV fluorescence from proteins and nucleic acids by shifting the emission into the green or red, as shown in the table in FIG. 5. This creates the opportunity for non-stained tissue contrast imaging at high resolution.

Figure 2:
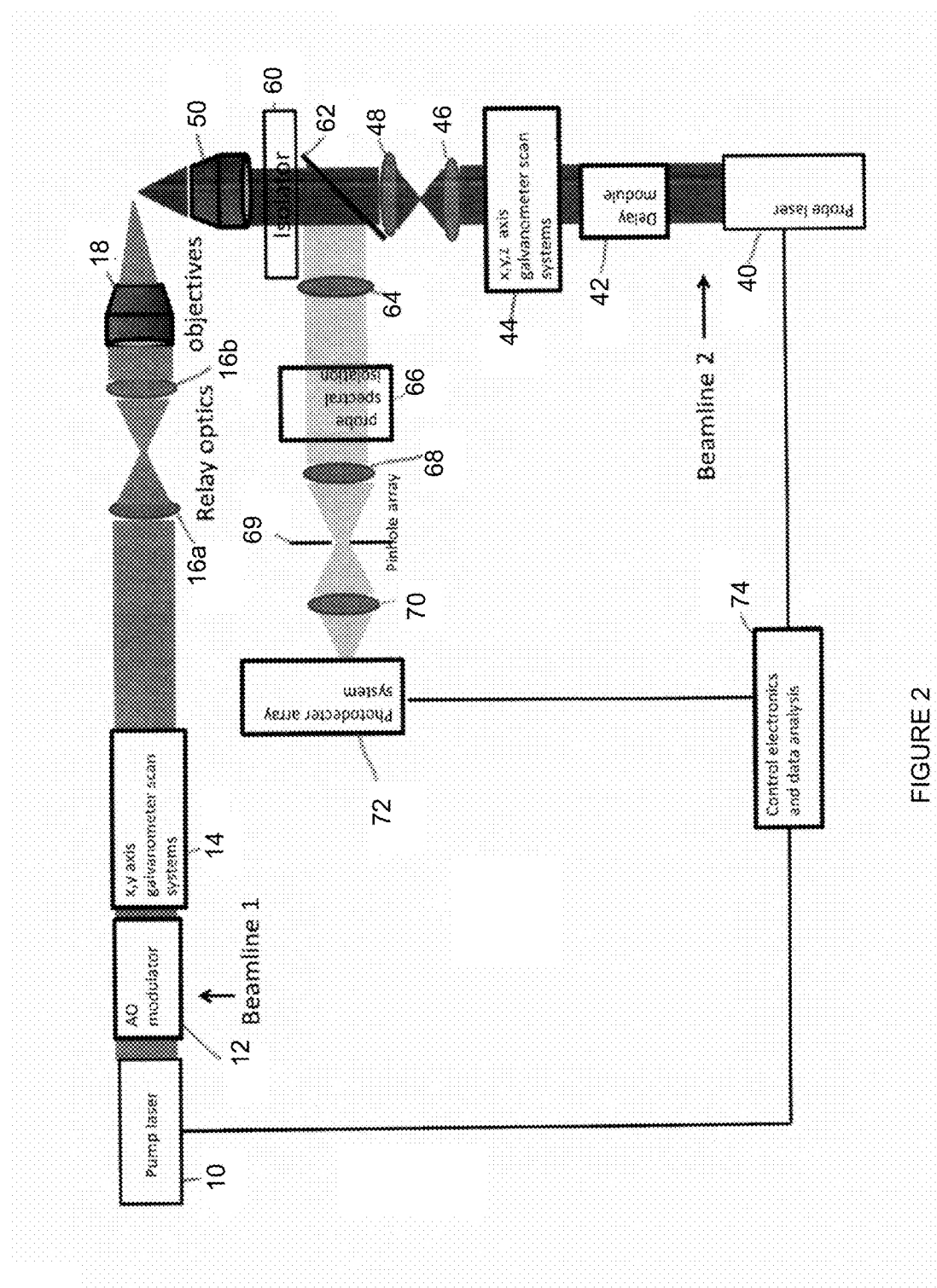
FIG. 2 is a block diagram of an example of a system used with the disclosed technology.

In the system disclosed here, for convenience called Orthogonal Confocal STEM (OC-STEM), there are two Point Spread Functions (PSF) that contribute to the final system response function called $PSF_{st}$. The basic system is shown in FIG. 2. One PSF is from the Gaussian beam pump illumination of the first beam line and is called PSFpu. The other is from the second beamline or probe beamline and is called $PSF_{pr}$. For the system $PSF_{st}=PSF_{pu} \times PSF_{pr}$.

Figure 3:
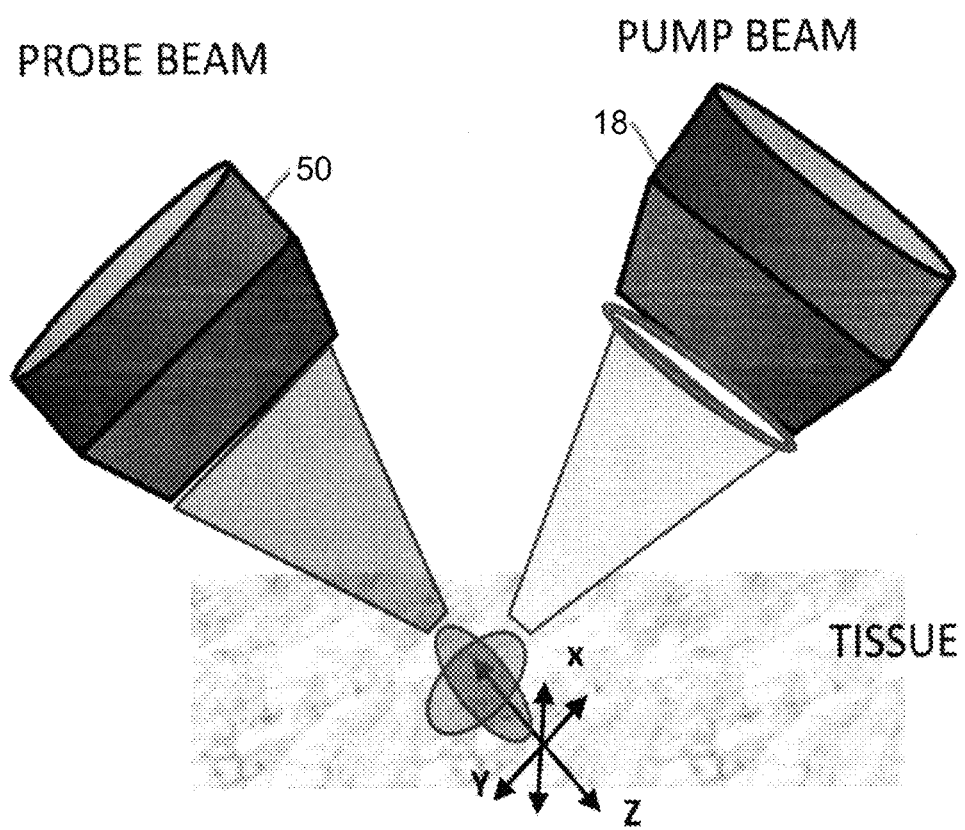
FIG. 3 is a block diagram of an example of a microscope objectives focal volume used with the disclosed technology.

The disclosed technology uses Gaussian pump illumination with a numerical aperture (NA) beam of greater than NA=1. This is shown schematically in FIG. 2 as the pump beam. The coordinate axes are shown in FIG. 3. The optical axis of the pump beamline is z, and the optical axis of the probe/detection beamline is y. The x axis is the one axis transverse to both beamlines.

Figure 6:
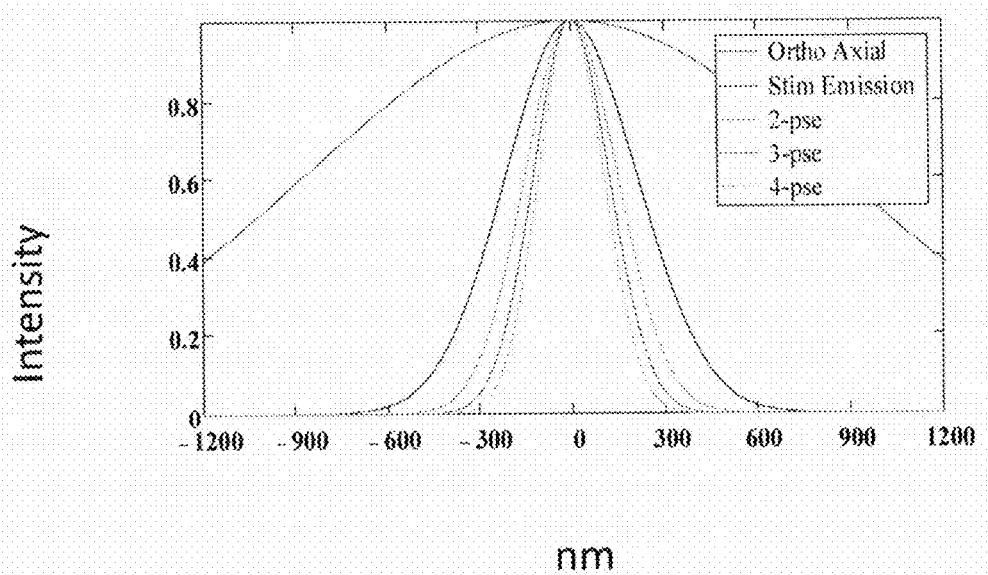
FIG. 6 is a plot of the intensity distribution in radius, along the axial z plane of the OC-STEM system for 1 pse (2 photons), 2 pse (4 photons), 3 pse (6 photons) imaging and 4 pse (4 photons) imaging.

In FIG. 6, shows the performance of the OC-STEM system along the z axis, which is the axial axis of the system. It can be seen the axial dimension of 1-4 photon OC-STEM is substantially less than the probe beam PSF which is also plotted in FIG. 6. In addition all the 1-4 photon PSFs ½ widths are less than ½ of the probe wavelength of 1380. This conditions creates significant dipole back scattered stimulated emission.

Figure 7:
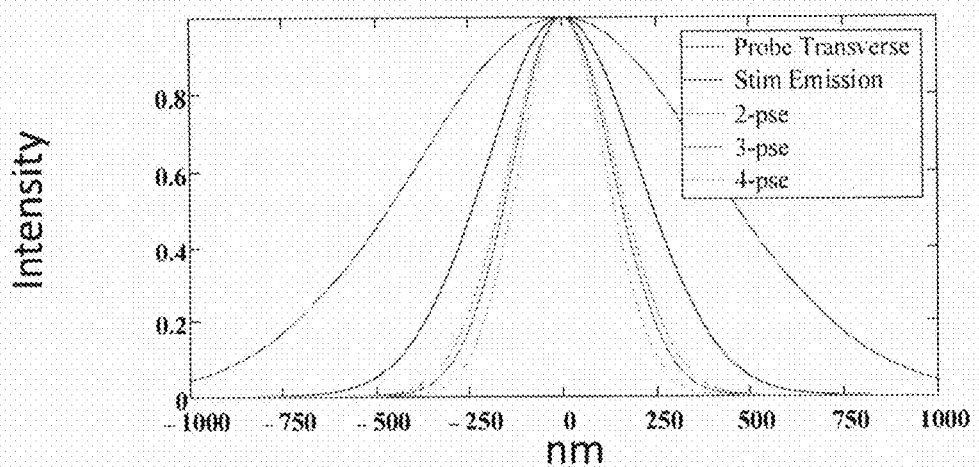
FIG. 7 is a plot of the intensity distribution in radius, along the transverse x plane of the OC-STEM system for 1 pse (2 photons), 2 pse (4 photons), 3 pse (6 photons) imaging and 4 pse (4 photons) imaging.

FIG. 7 shows the performance of the OC-STEM along the x axis, which is a transverse axis of the system. It can be seen the transverse dimension of 1-4 photon OC-STEM is substantially less than the probe beam PSF which is also plotted in FIG. 7. In addition all the 1-4 photon PSFs ½ widths are less than ½ of the probe wavelength of 1380. Thus the system will show sub-wavelength resolution in one transverse direction. The resolution in y direction will be a little less than the x direction, because the full axial dimension of the pump beam is used in imaging.

When the emission spot is reduced to less than 50% of the probe wavelength along the optical axis, dipole-like stimulated emission with both a forward and backward scattered lobe starts to occur as shown in FIG. 8. Backscatter occurs because of the lack of destructive interferometric cancellation of backscatter in gain lengths shorter than 50% of the emission wavelength. Direct backscatter enhances the recorded signal to noise ratio (SNR) of images because of reduced backscatter noise compared to forward propagating addition stimulated emission of the forward propagating probe beam.

MP-STEM systems operate near saturation where typically at most 36% of the excited molecules at focus will emit stimulated emission gain photons. STEM lasers systems have operated with very high repetition rate systems ~80 MHZ (12 ns pulse repetition rate) to build up SNR for lock-in detection of single photon STEM emission from rapid decay species, with imaging acquisition in the forward scattered direction or for multiple backscatter for collection in the epi direction. (Standard Multi-photon fluorescent systems operate at slower repetition, put higher intensities (near saturation) at focus.) At high repetition rates, near saturation local tissue heating can be an issue. Therefore lower repetition rates can be desired. However, in the backscattered direction repetition rates can be reduced because of the reduction in background photon noise.

At high repetition rates in MP-STEM systems, the excited state of long lived fluorophores cannot be fully depleted when the next pump—probe pair arrives. For molecules with fluorescence lifetimes of >2 nsec, such as NADPH, this can be a problem.

Above 1000 nm the photon damage limit in tissues is higher, enabling higher intensity focal spots than visible light. The focal spots can be smaller enabling enhanced dipole backscatter. Fiber lasers can be used for excitation and stimulated emission. Use of fiber lasers reduces the cost of system construction, and enhances ease of use. Tissue dispersion is lower above 1000 nm than below, making achieving a more precise focal spots with short pulses easier to achieve.

Below 950 nm NIR enhanced silicon diodes can be used to collect backscattered stimulated emission images. Use of photon wavelengths longer than 950 nm typically requires the use of detectors that are not silicon based. Array detectors are available with photodetectors formed from SiGe, InGaAs and HgCdTe, that can cover the wavelength band from 950 nm-1800 nm.

The fluorescent molecule energy level diagrams for STEM imaging are outlined in FIG. 1a. In STEM, two laser beams at the pump frequency, $\omega_{pu}$, and probe frequency, ωpr, are coincident on a sample as shown in FIG. 1a. The pump photon excites an electron into state S1. This exited stated decays via a Kasha process to the lowest level excited state S2 in 0.1-1.0 ps. The probe frequency photons have appropriate energy to drive an excited electron into a high level excited state in the ground state manifold S3 as shown FIG. 1a. The electron in the ground vibrational excited state then losses energy as it decays into the lowest ground state S0 by another Kasha process.

FIG. 1b shows the excitation of the fluorescent molecule into the electronic excited state via a 2-photon excitation process. The electronic excited state excitation occurs through a virtual level intermediate, which has a femtosecond lifetime. Therefore, the two excitation photons arrive close in time, which requires high photon intensities and occurs at high probability at the focal spot of the microscope, using high power picosecond or sub-picosecond laser pulses. Advantages of 2-photon excitation can include 1) the lower energy photons used in 2-photon excitation generally have lower absorption and scattering cross-sections than the 1-photon excitation energies, enabling deeper tissue excitation; 2) the requirement of high intensity of excitation enables emission mostly from the focal volume; 3) the lower energy photons produce less photo-bleaching molecules in the focusing and defocus cones of the microscope objective, providing less damage to the tissue being imaged.

FIG. 1c shows the energetics of a 4 photon MP-STEM process disclosed here. In this case 2-photon excitation and 2-photon stimulated emission are used. The addition of 2-photon stimulated emission along with 2-photon excitation is enabled by the approximate equivalence of the Einstein absorption and stimulated emission constants. The system is efficient when both the excitation and stimulated emission processes operate near saturation. This process is called 2 photon stimulated emission (2 pse) MP-STEM.

The addition of 2-photon stimulated emission has several advantages including; 1) less absorption, and scattering of stimulated emission photons, enabling rapid and deeper stimulated fluorescent imaging; 2) enables forward and backscattered STEM imaging of fluorescent transitions in the UV, which normally would not be observable because of tissue absorption; 3) enables imaging of short lived fluorescent molecules such as DNA and proteins.

FIG. 1d shows the energetics of 6 photon MP-STEM process, which is also disclosed here. In 3-photon excitation and 3-photon stimulated emission there are 2 intermediate virtual levels. Therefore the required incident laser intensities can be higher than in 2 photon excitation and 2 photon stimulated emission. However, the process enables incident photons in the near infrared, for UV or blue fluorescent transitions from deep within tissue. This process is called 3 photon stimulated emission (3 pse) MP-STEM. Four photon stimulated emission (4 pse) MP-STEM is also possible.

It should be noted that it is possible to mix pumping or probing with n photons with pump or probe beams with n−1 photon processes. Two photon excitation and 3 photon stimulated emission can be used to get a clean backscattered signal.

Referring to FIG. 2, a microscopy system 100 can have a pump laser 10 being focused along beamline 1 and a probe laser 40 being focused along beamline 2. Beamline 1 and beamline 2 are focused to a confocal region in a sample. The pump and probe beams can be produced by fiber lasers, or solid state lasers such as a Ti: Sapphire laser. The lasers beam photons can be in the green through near infrared regions of the optical spectrum (500-1840 nm).

Beamline 1 can include an Acousto-optic Modulator 12 that turns the beam on and off during image scanning to enable lock-in or differential stimulated emission detection. Further Beamline 1 includes a galvanometer scanning module 14 that scans the z axis line illumination the y axis to create a 2-dimensional image and in the x axis to create a 3-d volume of excitation. Beamline 1, the pump beamline, creates a Gaussian pump beam in the focal region.

The probe beam is delivered by the beamline 2, into a Gaussian focus that is confocal with the pump focus of Beamline 1. Beamline 2 can include a delay module 42 that can delay the probe beam from 0.001 femtoseconds to multiple nanoseconds after the arrival of the pump beam. The delay in the delay module 42 can be generated by a delay in the probe beamline or by electrical delay in a trigger circuit used in time synchronization of the pump and probe pulses. The pathlengths of the probe can initially be adjusted by placing an optical delay with movable mirrors in the laser beams, as illustrated for the probe beam. Long time delays can be used when the system is used to measure fluorescence lifetime of biomolecules.

Multiple delays can be used to measure a multi-component exponential delay curve. One can measure multiple delays at each pixel as the laser is scanned, in order to enhance image acquisition speed. This is accomplished by using an optical switch (not shown) in the probe beam line to switch the pulse between two or more delay lines.

Beamline 2 can include a galvanometer scanning module 44 capable of filling in the array of spots of the light sheet and scan in the orthogonal direction to produce a full image.

The backscattered stimulated emission probe light can be collected in beamline 2 and is focused through a pinhole 69, a differential or lock-in photon signal processing system. The probe beam must also be scanned by the galvanometer system 44 in Beamline 2. The scanning systems 14, 44 in beamline 1 and beamline 2 may be locked together to create overlapped beams as they scan through the tissue. A sample to be investigated is located in or near the focal volume of the two beamlines. In addition Beamline 2 includes an optical delay module 42 to control the time of arrival of the probe pulse relative to the pump pulse.

Multiphoton illumination uses pulses shorter than one picosecond, with short coherence lengths. SRS may also use lasers as long as 5 nanoseconds to provide narrow vibrational excitation. The data is collected and the laser timing and diagnostics are controlled by a control electronics module 74.

When MP-STEM is used for deep tissue imaging, the small refractive index and thermal gradients in the tissue can reduce the focal intensity of the pump beam on target. In this case an optical aberration correction system (not shown) can be used to enhance the focal power. These systems have been used in CARS and Multiphoton fluorescent microscopy systems.

The stimulated emission microscope system 100 described here is a bright field imaging system and the intensity of the background probe radiation can be calibrated on a rapid time interval cycle. Therefore, the pump Beamline 1 has an optical modulator 12 that turns the pump beam on and off enabling collection of probe beam photons with and without probe beam gain from stimulated emission. This optical modulator 12 can be an acousto-optic modulator.

Figure 4:
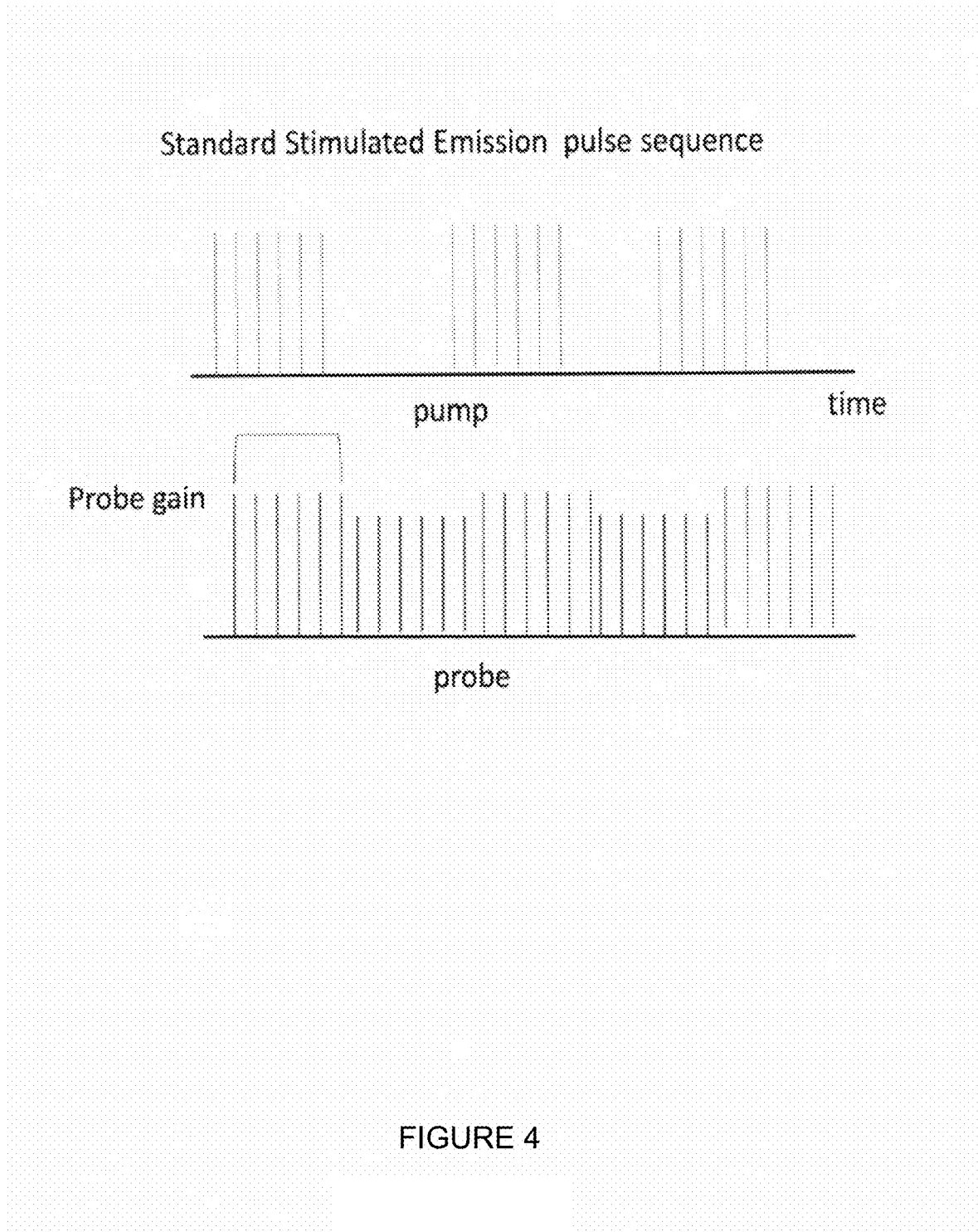
FIG. 4 is a graphical depiction of a time sequence for pump and probe beams.

The time sequence of the pump and probe beams are shown in FIG. 4. The pump is turned on for a series of pulses to measure gain and turned off to measure the bright field single without gain. The repetition rate of the pump and probe can be about 10-20 MHz. for MP-STEM and some 1 photon fluorescence STEM applications. For some 1 photon fluorescence STEM and stimulated Raman applications the repetition rate may be 80 MHz. The photodetector array system 72 can be a lock-in array amplifier system and can measure the envelope frequency of the pulse train at about 1-5 MHz. It should be noted that because of the reduced backscattered noise high dynamic range non lock-in detection arrays can also be used for image acquisition.

In FIG. 2, the stimulated signal can be collected by a detector 72 in the backscattered direction. The probe wavelength and stimulated emission backscattered wavelength are substantially the same. Thus changing polarizations are used to isolate the back reflected signal. The probe beamline thus has an isolation module 60 that controls back reflected photon polarization to collect the backscattered photons. The isolation module 60 can be composed of a Faraday rotator and a waveplate, and the pickoff mirror 62 for the beam line is a polarization dependent reflector. For very deep tissue imaging using dipole backscattered emission, the signal is collected in the imaging aperture 68, 70 and with a confocal pinhole array 69, in front of the collection detector array 72, as shown in FIG. 2. This isolates multiple scattered photons.

The time sequence of pump and probe beam signals are shown in FIG. 4. The imaging signal corresponds to the stimulated gain in intensity of the probe beam, computed as the difference between the probe signal from the fluorescent molecular excited state populated by the pump beam, and the un-excited molecular probe signal with the pump beam off. Standard interference filters can be used to separate pump and probe photons because they are separate in wavelength by >10 nm.

FIG. 5 provides a table of pump and probe wavelengths for 1, 2 3 and 4 photons for both excitation and stimulated emission in STEM and MP-STEM for proteins and DNA as well as two electron transport cofactors NADH and FAD, widely used in cellular metabolic imaging. For proteins and DNA, the single photon pump and probe wavelengths are in the deep UV and cannot be imaged efficiently and usually without tissue damage in-vivo. With 2-photon excitation and emission MP-STEM imaging the wavelengths are moved into green and red, suitable for imaging with a depth of about 100 microns or so. Using 3-photon emission MP-STEM imaging, proteins and DNA can be imaged in near infrared, at depth of 300 microns or more.

The electron transport cofactors NADH and FAD can be imaged in the near IR with both 2 and 3 photon excitation and emission MP-STEM imaging. With 3 photon imaging, image depth approaching one millimeter can be achieved enabling in-vivo examination of tissue metabolism to a depth of up to 1 millimeter. A 4-photon excitation process for certain molecules move the excitation window far into the IR, where water absorption increases.

For depth in in-vivo MP-STEM imaging, the water windows at 1300 nm and 1650-1850 nm can be used. In these wavelength ranges images down to 1 mm and more can be obtained. As shown in the Table in FIG. 5, MP-STEM imaging with 3 or 4 photons, from the pump and probe beams can be used for the electron transport cofactors. The limit in IR wavelength is due to the increasing water absorption above about 1800 nm.

FIG. 6 shows the axial (along the optic axis of the microscope) and FIG. 7 shows transverse (in the image plane of the detection microscope focus) $PSF_{st}$ of an OC-STEM system using 1-4 photons for pump excitation and probe stimulated emission. The pump wavelength of 1020 nm and a probe wavelength of 1380 nm. The pump has an NA of 1.1. In this system the probe/detection microscope system has a numerical aperture (NA) of 0.9.

Plotted in FIG. 6 are the axial $(PSF_{st})$'s for the probe beam, a STEM system, a 2 pse MP-STEM system, a 3 pse MP-STEM system and a 4 pse MP-STEM system. The PSF of the one photon STEM system is about 50% of the probe wavelength enabling some dipole-like backscatter imaging. The PSF of the 2 pse system axial ½ width is about 31% of the probe wavelength enabling more dipole-like backscatter. The axial $PSF_{st}$ of the 3 pse system is about 25% of the probe wavelength. As shown in FIG. 9 single and multiple OC-STEM systems produce dipole backscatter.

The transverse resolution along the x axis is shown in FIG. 7. The somewhat lower y axis resolution is not shown.

In the implementations and methods disclosed here, the use of MP-STEM imaging can determine the molecular fluorescent lifetime by measuring the signal with two or more temporal delays between the pump and probe laser pulses. Two different time delay measurements can be used to measure the molecular concentrations with a single decay constant. This process is called stimulated emission Fluorescent Lifetime Microscopy (seFLIM).

Stimulated Fluorescent, MP-STEM and OC-STEM Theory

The absorption cross section, $\sigma_{abs}$, for optical radiation for a single chromophore at room temperature is about $10^{-16}$ cm². In a tightly focused laser beam with a beam waist, S (~$10^{-9}$ cm²) the integrated intensity attenuation of the excitation pump beam $\Delta I_{pu}/I_{pu}$ is proportional to the ratio between $\sigma_{abs}$ and S, where $I_{pu}$ is the intensity in the excitation pump beam as shown in Eq 1:

$$\Delta I_{pu}/I_{pu} = -N_0 \sigma_{abs}/S \qquad (1)$$

$N_0$ is the number of molecules in the ground state. For a single chromophore, $\Delta I_{pu}/I_{pu}$ is of the order of $10^{-7}$. The stimulated emission cross section, $\sigma_{stim}$, is comparable to the $\sigma_{abs}$, and the change in intensity of a stimulated probe beam $I_{pr}$ is:

$$\Delta I_{pr}/I_{pr} = -N_2 \sigma_{stim}/S \qquad (2)$$

$N_2$ is the small number of molecules transiently probed by the stimulating probe beam. For a single chromophore $\Delta I_{pr}/I_{pr} = 10^{-7}$.

Normally, SEM is conducted in a non-saturating condition of the four-level system (FIG. 1a). Under this condition, $N_2$ in equation (2) originates from a linear excitation: $N_2 \propto N_0 I_{pu} \sigma_{abs[0 \to 1]}/S$. This relation, together with equation (1), indicates that the final signal $\Delta I_{pr}$ is linearly dependent on both $I_{pu}$ and $I_{pr}$:

$$\Delta I_{pr} \propto N_0 I_{pu} I_{pr} (\sigma_{abs[0 \to 1]}/S)/(\sigma_{stim[2 \to 3]}/S) \qquad (3)$$

The MPE and MP-STEM each require two or more photons to interact simultaneously with the fluorescent molecules. However, in MP-STEM the two processes of excitation and stimulated emission can be separated in time by 0.3-4000 ps, and thus can initially be considered to be independent. The time scale of the "simultaneous" arrival of the photons is determined by the intermediate virtual lifetime $\Delta \tau \approx 10^{-16}$ s (as per the uncertainty principle). Hence, a 2-photon cross section $(\sigma_2)$ is about $10^{-49}$ cm⁴ (s/photon) (or $A^2 \Delta \tau$), a 3-photon cross section $(\sigma_3)$ is about $10^{-82}$ cm⁶ (s/photon)² (or $A^3 \Delta \tau^2$) and a 4-photon process is about $10^{-115}$ cm¹⁰ (s/photon)³ (or $A^4 \Delta \tau^3$). These small cross sections require higher incident laser focal intensities, and shorter pulses in MP-STEM than single photon SEM. Pulses of less than 100 fs/pulse are often used. This is true for both the pump and probe beams.

Only one MP-STEM emission process/molecule/pulse can occur. Therefore the pump pulse can operate very close to saturation at focus of the transition to achieve the maximum population in the excited state, and to increase the probability of the stimulated emission pulse to de-excite pumped molecules. In saturation about 40-50% of the molecules at focus can be transferred to the excited state during the 100 fs excitation pulse, thus $N_2 \approx N_0/2$, and:

$$\Delta I_{pr} \propto N_0 I_{pr}/2 (\sigma_{stim[2 \to 3]}/S) \qquad (4)$$

An n-photon excitation or emission process is proportional to $\sigma_n I_{peak}^n \tau$, where $I_{pk}^n$ is the pump or probe peak intensity, $\sigma_n$ is the n photon cross section, and $\tau$ is the pulse length. For a square pulse in time at saturation: $\sigma_n I_{peak}^n \tau = 1$. Therefore, the saturation peak intensity for the pump beam is:

$$I_{pks}^n \approx (\sigma_n \tau)^{-1/n} \qquad (5)$$

The probe beam can operate at the high end of the linear gain curve to enable computation of molecular concentrations that require a linear relationship of the gain and the concentration. This occurs at about 50-60% of saturation.

Using diffraction limited focusing geometry, the relation between the average incident photon flux ($P_{avg}$, in units of photons/s) and $I_{peak}$ is:

$$P_{avg} \approx (0.61)^2 \lambda^2 (f \cdot \tau) I_{peak}/(NA)^2 \qquad (6)$$

where f is the pulse repetition rate. Combing Eq. 6 and the saturation power for the n photo process ($p_{avg}^{ns}$) can be estimated as:

$$P_{avg}^{ns} \approx (0.61)^2 \lambda^2 (f \cdot \tau) \cdot (\sigma_n \tau)^{-\frac{1}{n}}/(NA^2) \qquad (7)$$

The maximum intensity at focus in practice is limited by optical breakdown of the tissue and is wavelength dependent. The pulsed optical damage threshold measured for photon wavelengths above 1 μm for 100 fsec pulses has been shown to be about $2 \times 10^{14}$ W/cm², or about 20 nJ/μm²/(100 fs pulse). Below 1 μm wavelength the damage threshold increases. With a high NA (1.3) objective lens, a Gaussian focal spot and 100-fs pulses at 80-MHz repetition rate and 1.0 um excitation wavelength, the estimated saturation powers for one, two, three, and four-photon processes are, respectively, ≈0.3 mW (0.1 nJ/pulse), ≈30 mW (1 nJ/pulse), ≈150 mW (5 nJ/pulse), and ≈300 mW (10 nJ/pulse) by Eq. 8 and the excitation cross sections estimated above. Thus in the limit the damage threshold for 2 pse and 3 spse is more limited by average power of the pump and probe beams than the damage threshold for 70-100 fs NIR pulses. However for the lower NA objectives used in OC-STEM the energy/pulse and the average energy of the laser can be increased to enable maximum backscattered signal. The required saturation power scales as $1/NA^2$ as shown in equations 6 and 7. Therefore, the Gaussian probe beam power can be increased by about 1.8 times in going from a 1.2 to a 0.9 Gaussian beam. In the Bessel probe beam, the narrowness of the central lobe compensates for the lower NA used. However, how the laser energy is distributed to the annular illumination zone has an effect on the laser power required.

The laser power used will have to be increased for imaging at 1-3 absorption/scattering depths. At 800 nm, the absorption depth in tissue is 120 μm, at 1000 nm wavelength the absorption depth in brain tissue is ~200 μm, and at 1300 nm the absorption depth is 300 μm. Therefore it is advantaged to operate above 1 micron in pump wavelength. MP-STEM can operate at about 0-3 absorption depths (15% transmission to focus for the pump wavelength). Thus the maximum incident estimated laser power for two and three-photon processes are, respectively, ≈600 mW (20 nJ/pulse) and ≈3000 mW (100 nJ/pulse) at the surface. These average powers are high. It is sometimes better to operate at a reduced laser rep rate of 10 MHz. Reducing the laser repetition rate can have an effect on the lock-in photon detection protocols. However, with the lower backscatter noise, and use of a differential detection imager, the use of low repetition rate laser systems can be used.

The Point Spread Function of a MP-STEM system ($PSF_{MP-STEM}$) scales as the single photon illumination Point Spread Function ($PSF_{il}$) to the power equal to the number of photons in the process. The pump PSF ($PSF_{pu}$) and probe PSF ($PSF_{pr}$) are each raised to the power of the number of photons used per each electronic transition, n, and are multiplied together to produce the $PSF_{MP-STEM}$ as shown in eq (8).

$$(PSF_{MP-STEM}) = (PSF_{pu})^n \cdot (PSF_{pr})^n \qquad (8)$$

FIGS. 6 and 7 show the PSFs in both the axial and transverse direction for the probe beam, the standard STEM probe stimulated emission spot as well as the 2 pse, 3 pse and 4 pse MP-STEM stimulated emission spots, for a 1.1 NA probe objective, and objective wavelength of 1380 nm. The pump beam uses a 1.1 NA objective and a probe wavelength of 1020 nm. These wavelengths are useful for 3 pse from NADH and are used throughout the examples given below.

It is known that a single fluorophore will emit stimulated emission into the backward illumination and forward propagating modes into the stimulating mode with equal probability. The fluorophore is small relative to the optical wavelength and cannot tell the direction of propagation of the field. However, as the stimulated emission gain length increases the backscatter decreases. Although the gain in the stimulated field is small in microscopy because of the small focal spot, as the probe beam propagates along the forward direction through the focal spot the stimulated emission photons add in phase, increasing the coherent traveling field. The stimulated emission in the back propagation direction adds out of phase as the incident beam propagates forward. Thus as the gain medium length increases, the backscattered stimulated emission photons from axially spatially separate fluorophores destructively interfere. The backscatter stimulated field quickly decreases over sub-wavelength dimensions. This small sample coherent backscatter is related to the small structure backscatter in Coherent Anti-Stocks Raman Scattering.

The forward and backscattered fields generated along the optic axis can be modeled over the focal spot of length $2Z_1$ by the following equation:

$$G_{(f,b)}(t) = \int_{-z_1}^{z_1} C(z) E_{pr} Re\{e^{-i(kx + w_{pr}t + \theta(z))}\} PSF_{axial}(z) dz \qquad (9)$$

$G_f$ is the forward far field electric field gain, and $G_b$ backward far field electric field gain. $E_{pr}$ is the probe electric field, $\omega_{pr}$ is the probe frequency, k is the propagation constant and $\theta(z)$ is the phase of the emitted photons at each point. C(z) is the gain factor that depends on the local concentration of fluorophores and stimulated emission cross section. It is assumed that in the forward direction $\theta(z)=0$ for all points, as the stimulated photons add in phase. In the backward propagating direction $\theta(z)$ is different at each point as the there is a time change for the emission of each axial point. It assumes that z=0 is at the center of the $PSF_{axial}(z)$, and at that point $\theta(z)=0$.

FIG. 8 plots the ratio of the forward to backscattered electric field gain ($G_f/G_b$) for a Gaussian distribution of excited states along the optic axis as a function of the ratio of stimulating wavelen8gth $\lambda_{pr}$ to Gaussian ½ width, w, that is ($\lambda_{pr}/w$). For $\lambda_{pr}/w>8$ the backscatter gain approaches the forward gain, while for $\lambda_{pr}/w<1.5$ the backscatter approaches zero. The total Gain is thus $G_f+G_b$, when $\lambda_{pr}/w>8$, $G_f=G_b$.

For a uniform volume of emitters the optimum signal is achieved for a $\lambda_{pr}/w \approx 4-5$. For larger $\lambda_{pr}/w$ ratios, the emission spot is small and the number of emitters present produces weak stimulated emission. The PSF of the one photon STEM system achieves a $\lambda_{pr}/w \approx 2.4$. This will result in backscatter equal to about 15% the forward scatter enabling some dipole-like backscatter imaging. The axial $PSF_{st}$ of the 2 pse system achieves $\lambda_{pr}/w \approx 3.2$. The axial $PSF_{st}$ of the 3 pse system achieves $\lambda_{pr}/w \approx 4.0$. Thus the OC-STEM results in measureable dipole backscatter for STEM and MP-STEM illumination and detection strategies.

In a confocal microscope, backscatter dipole emission from a focal spot with less than ½ wavelength axial dimension, while the background noise comprises backscattered probe photons from refractive index (RI) gradients in the focal volume and multiple backscattered photons back that make it into the confocal aperture. RI noise is at most about $5\times10^{-4}$ of the incident beam, at the interface of cytoplasm and cell nuclei. Thus backscatter noise is less than forward scatter noise. The signals and sources of forward and backscattered signals and noise are summarized in FIG. 8.

Dipole-like scattering is particularly important in deep tissue imaging. This enables much more signal light and fewer background photons to be collected in the illumination aperture of the microscope. In addition it provides a confocal scattering image of the tissue understudy, enabling at least two forms of imaging with each image scan-scattered photon imaging and stimulated emission imaging. These two imaging modes can coherently interfere with each other.

One can calculate the sensitivity, and the required pixel dwell time for a high speed MP-STEM and OC-STEM system. The largest signals are achieved for pumping at saturation, and stimulated emission probe at near 60% of saturation. At pump saturation 50% of the molecules at focus will be in the lowest excited state after decay from the upper pumped level. With 100 fs pump pulses we assume no decay out of the pumped levels during the pulse. The maximum photo-pumped population is 50% given the equivalence of the Einstein emission and absorption coefficients. However in the probe beam, it is desirable to provide stimulated emission gain that is in the linear range to provide an accurate measure of the concentration of emitters.

Again because the probe pulse is about 100 fs there is minimal decay from the upper and lower excited states during the probe pulse and about 50% of the molecules will be in each the upper and lower level of the transition. Thus the probe intensity can be below the stimulated emission saturation intensity, e.g., the probe beam intensity can be about 60% of fluorescent saturation, in order to maintain linearity of probe gain.

For a 3 spe system designed to detect NADH at a 20 MHz laser pulse repetition rate, and a 2 MHz sample window (~10 pulses/sample window) in the ≈100 mW (2.0 nJ/pulse) 1020 nm pump region and ≈120 mW (1.2 nJ/pulse, $8.6\times10^9$ photons/pulse) 1380 nm probe region. The power at the surface varies from the focal power numbers to about 10 times higher depending on the focal depth.

The pump power is in saturation and the probe power is at the high end of the linear gain region. For the probe at 20 MHz laser repetition rate about $8.6\times10^{13}$ photons in 10,000 pulses are delivered per pixel/(500 µs dwell time). Half of the probe pulses are delivered with the pump pulse off. In the 5,000 pulses with both probe and pump on, each molecule can be excited at most 5,000 times (once per pulse) if the pump power drives molecular transitions into saturation. In addition, in the limit 2,500 stimulated emissions are backscattered for a small volume of emitters. The maximum backscattered noise (such as at the cell nucleus interface) is about $2.1\times10^9$, thus the backscattered noise/pixel dwell time with the pump on (or off) per pixel is about $4.6\times10^4$ photons. The signal is in the linear part of the probe gain curve, and thus about 2,500×n gain photons/molecule can be added to the probe gain/pixel dwell time. Thus in the limit in a high noise pixel, when n=3 about 6 molecules signal equal to RI gradient noise. Thus a dynamic range of $10^5$ achieved with a lock-in amplifier array system can detect 10 molecules/pixel. If 2000 molecules contribute to the backscattered signal then a standard imager with a dynamic range of 1000 would be adequate.

For the system parameters in FIG. 7, the ½ width of the focal ellipsoid is ~0.03 µm³, and the required emitter concentration for high SNR rapid scanning is below the mM range. This is less than to the concentration of NADH in cells. In mitochondria, the concentration of NADH is higher.

In stimulated coherent spectroscopy, the detected signal can be described in terms of classical wave interference in the far field. The induced signal field $E_s$ of frequency $\omega_s$, is generated at point r through a nonlinear process and is detected at a far-field point R. At the detection point, the induced field is mixed with a local oscillator field $E_{LO}(R)$, which is phase coherent with the former. The total intensity at the far field detector is then written as:

$$S(R) = \left(\frac{n(\omega_s)c}{8\pi}\right)|E_s(R) + E_{LO}(R)|^2 = I_s(R) + I_{LO}(R) + \frac{2n(\omega_s)c}{8\pi}\text{Re}\{E_s(R)\cdot E^*_{LO}(R)\}$$

where $n(\omega_s)$ is the refractive index of the material at frequency $\omega_s$, c is the speed of light, and $I_s$, $I_{LO}$ are the intensities of the induced signal and the local oscillator fields, respectively.

The fields E(R) are complex with a given wave vector that depends parametrically on R. The heterodyne contribution to the signal through which stimulated coherent optical signals can be understood is shown in Eq. (10)

$$S_{het}(R) = \frac{2n(\omega_s)c}{8\pi}\text{Re}\{E_s(R)\cdot E^*_{LO}(R)\} \tag{10}$$

The excitation field provides the local oscillator that interferes with the signal field in the far field.

Coherent stimulated multiphoton processes can be analyzed in terms of the third, or higher, order molecular susceptibility. MP-STEM is different from SRS because the pump beam does not coherently participate in the multiphoton stimulated emission process. The Kasha decay from the pumped excited band into the lowest excited state and the variable delay between the pump and probe pulses causes a loss of coherence between excitation and stimulated emission processes. However, the pump does contribute to the process by creating the population of excited states that participate in stimulated emission.

In forward scattered MP-STEM the signal of interest is the probe gain field $G_{pr}(r)$ or the signal field $E_{si}(r)$, which depends upon the induced polarization, $P_{pr}''(\omega_{pr}, r)$, generated at focus, where n is the number of emitted probe photons per event, and is described by Eq. 11, $$P_{pr}''(\omega_{pr}, r) \propto |E_{pr}(r)|^{2n-2}\cdot E_{pr}(r)\cdot I_{pu}^n(r)\cdot e^{-\Delta t/\tau}\cdot\chi^{2n-1}(\omega_{pr}, r) \tag{11}$$

Here $\chi^{2n-1}(\omega_{pr}, r)$ is the molecular susceptibility of the medium for the relevant order of susceptibility. $E_{pr}$ is the probe electric field, $I_{pu}$ is the pump intensity, and $\Delta t$ is the delay between the peak of the pump pulse and the peak of the probe pulse, τ is the excited state decay constant.

In 2 photon excitation and stimulated emission processes a third order susceptibility is used, while in 3 photon excitation and stimulated processes a fifth order susceptibility is require.

The induced electric field $E_{si}$ generated at point r near focus is detected at a far field point R where it is mixed with a local oscillator field that is phase coherent with the induced field. In the forward direction the local oscillator field is $E_{pr}$, while in the backscatter direction the local oscillator field is the index gradient backscatter field $E_{bs}$ as shown in FIG. 9. A spatial phase shift for the measured field at a detection point R relative to the phase at the excitation point r can occur, which depends on the excitation and detection geometry. For forward scatter it is assumed that $\phi$ is the spatial phase of the induced field at R relative to the phase at the origination point r, and $\alpha$ measures a similar spatial phase shift between r and R for the probe local oscillator field. These relations are shown in Eq. 12 and Eq. 13

$$E_s(R) \approx P_n(\omega_{pr}, r) e^{-i\phi} \tag{12}$$

$$E_{LO}(R) \approx E_{pr}(r) e^{-i\alpha} \tag{13}$$

The stimulated field in a MP-STEM microscope be using eq. 12 and eq. 13;

$$E_s(R) = P_{pr}^n(\omega_{pr}, r) \propto |E_{pr}(r)|^{2(n-1)} \cdot E_{pr}(r) \cdot I_{pu}^n(r) \cdot e^{-\Delta t/\tau} \cdot \chi^{2n-1}(\omega_{pr}, r) \cdot e^{-i\phi} \tag{14}$$

When the stimulated emission from a plane of dipoles perpendicular to the direction of field propagation, is measured in the far field, there is $\phi = -\pi/2$ radian change in the phase between the dipole emission plane and the far field. When a single dipole is present at focus, the induced field exhibits a phase that is spatially invariant, i.e., $\phi=0$.

In a MP-STEM microscope the scattering volume can be treated as a dipole, as it is less than a wavelength in the transverse dimensions. Therefore in the far field, $\phi=0$. Thus the heterodyne term in the forward far field for a dipole at focus is shown in Eq. 15

$$S_{pr}^n(\omega_{pr}, R) \propto [I_{pu}(r)]^n \cdot e^{-\Delta t/\tau} \cdot |E_{pr}(r)|^{2(n-1)} Re\{ \cdot E_{pr}(r) \cdot E_{pr}^*(R) \cdot \chi^{2n-1}(\omega_{pr}, r) \} \tag{15}$$

This relation contains the term $E_{pr}(r) \cdot E_{pr}^*(R)$ which carries phase information that depends solely on the spatial profile of the excitation field. Using Eq. 13, this latter term can be rewritten as $|E_{pr}(r)|^2 e^{i\alpha}$. The Gouy phase shift in a high NA microscope system from the focus to the far field is $\alpha = \pi/2$. We can thus write:

$$S_{pr}^n(\omega_{pr}, R) \propto [I_{pr}(r)]^n \cdot [I_{pu}(r)]^n \cdot e^{-\frac{\Delta t}{\tau}} \cdot \text{Im}\{\chi^{2n-1}(\omega_{pr}, r)\} \tag{16}$$

Eq. (16) describes the forward scattered gain in MP-STEM heterodyne signal with the small scatterer volume centered on the focal plane.

In MP-STEM backscatter signal detection, the local oscillator signal, when it is present, comes from probe beam reflection from refractive index field gradients and nanoparticles within the probe beam focus. The backscatter source can be anywhere within the single photon focus of the microscope, or the acceptance confocal pinhole aperture. Therefore, the effect of the Guoy phase, and focal position of the backscatter source and its interference with the MP-STEM signal can be considered. In deriving the backscatter field phase relative to the stimulated emission field we will follow the approach of Hwang and Moerner for nanoparticle scattering.

A nanoparticle can be modeled has having a real and imaginary scattering amplitude $\sigma/A + i\varphi$ where $\alpha/a$ is the real part responsible for absorption and $\varphi$ is the phase change associated with the transmission of a laser beam. After the nanoparticle, the probe field (with $e^{-i\omega t}$ assumed) is $$E_r(r) = E_{pr}(r) + E_{sc}(r) = E_{pr}(e^{ikr}) + \left(\frac{\sigma}{A}\right) E_{pr}(e^{ikr}) + i\varphi E_{pr}(e^{ikr}) \tag{17}$$

In the backscattered direction, the phase and refractive index gradient dependent scatter $E_{bsRI}(r)$ is of significance. Incorporating the phase of the induced backscatter, $\varphi_{sc}(z)$, $E_{bsRI}(r)$ is:

$$E_{bsRI}(r) \propto i\varphi E_{pr}(ikr + i\varphi_{sc}(r)) \tag{18}$$

This field interferes with the stimulated backscatter $E_{bsSE}(r)$. In order to calculate the far field signal, the contributions of the Gouy phase and the scatterer induced phase can be taken into account.

The Gouy phase shift of a 2 dimensional wavefront in a high NA microscope is a total of $\pi$ radians. The phase of the probe beam is described in FIG. 9. Near focus, at the distance z (z is positive for an advance in the propagation direction) on axis, the phase shift is given by $-\tan^{-1}(z/z_R)$, where $\omega_0$ is the beam radius at the focus (waist). The quantity $z_R$ is equal to $\pi\omega_0/\lambda_{pr}$, the Rayleigh range of the waist. This phase shift approaches a constant value of $\pi/2$ between the focal position and a large distance in the far field.

A forward scattered beam from a nanoparticle has a phase shift of $\pi/2$ radians both in the far-field and the near-field. That is, when a field is present at the input of a subwavelength aperture the phase change through the aperture is $-\pi/2$. Using Babinet's principle, when the complimentary point scatterer (absorber, or refractive index gradient) is present, in place of the aperture, the scattered beam undergoes a phase change of $+\pi/2$ radians. Thus in the far field $\varphi(R)$ is:

$$\varphi(r) = \pi - \tan^{-1}\left(\frac{r}{r_R}\right) \tag{19}$$

The far field in the backscatter direction $E_{bs}$ is the sum of the backscatter refractive index gradient phase change particle scatter, $E_{bsRI}$, and the backscattered stimulated emission $E_{bsSE}$.

$$E_{bs}(R) = E_{bsRI}(R) + E_{bsSE}(R) \tag{20}$$

The backscattered intensity is $$I_{bs}(R) \propto I_{bsRI}(R) + I_{bsSE}(R) + Re\{E_{bsSE}(R) \cdot E_{bsRI}^*(R)\} \tag{21}$$

The dipole induced backscatter is assumed to originate from the plane of focus, while the index gradient backscatter can originate anyplace near focus. Therefore the contribution of a variable Gouy phase is mostly contributed by the RI induced scatter. Secondly in the backscatter direction the stimulated emission experiences a 0 phase shift as it propagates in the backward direction. We also assume since the n photon process is phase matched and resonant, such that the $re\{\chi^{2n-1}(\omega_{pr}, r)\}=0$. Therefore using Eq 20 and Eq. 21 the heterodyne backscatter term $S_{bs}(R)$ is:

$$S_{bsv}(R) \propto \left[ [I_{pr}(r)]^{n-1} \cdot [I_{pu}(r)]^n \cdot I_{bsRI}^{\frac{1}{2}}(r) \cdot I_{bsRI}^{\frac{1}{2}}(r) \cdot e^{-\frac{\Delta t}{\tau}} \cdot \text{Im} \{\chi^{2m-1}(\omega_{pr}, r)\} \right] \left[ 1 - 2\varphi \sin\left(\tan^{-1}\left(\frac{z}{z_R}\right)\right) \right] \tag{22}$$

The backscatter from each pixel can have refractive index backscatter, stimulated emission backscatter or both. During the pulse train the presence or absence of back scatter can be determined by measuring the backscatter signal from pulses when the pump pulse is off. The position with the focus can be determined by interference of the backscatter with the pump off with a reference beam that can be used to focus the system. Many such approaches exist.

MP-STEM Signal Sensitivity and SNR

Large MP-STEM probe gain signals can be achieved when pumping at saturation. With 100 fs pump pulses, it is assumed there is no decay out of the excited state manifold in first 500 fs after the pulse. The maximum signals, for all fluorescent lifetimes, are achieved with a probe delay, $\Delta\tau_{pr}$, of about 0.5-1.0 ps.

The maximum photo-pumped population is 50% of the molecules at focus given the equivalence of the Einstein emission and absorption coefficients. It is desirable to provide stimulated emission gain that is in the linear range to provide an accurate measure of the concentration of emitters. Therefore, the probe beam intensity cannot produce saturation, but about 50% of fluorescent saturation.

The requirement for high spatial resolution for diffuse scatterers is unlikely unless there is a specific boundary near the resolution limit of the scan, such as in mitochondria. For concentrations of bound scatterers, the local concentration can be elevated. In cases like imaging RNA in ribosomes, many emitters can be present in a very small volume.

The concentration of NADH in cells is on average about 0.3 mM. The free to bound ratio of [NADH] ranges from 1-4. Bound molecules in mitochondria can have concentrations that are higher than average and thus can yield acceptable signals. To achieve acceptable signals of diffuse distribution of free NADH can require averaging over about 25 pixels or a cube about 5 pixels on a side or a length or about >2µ diameter if they are laid out on a square grid separated by the ½ width of the PSF.

Stimulated Raman Scattering OC-STEM

Figure 10:
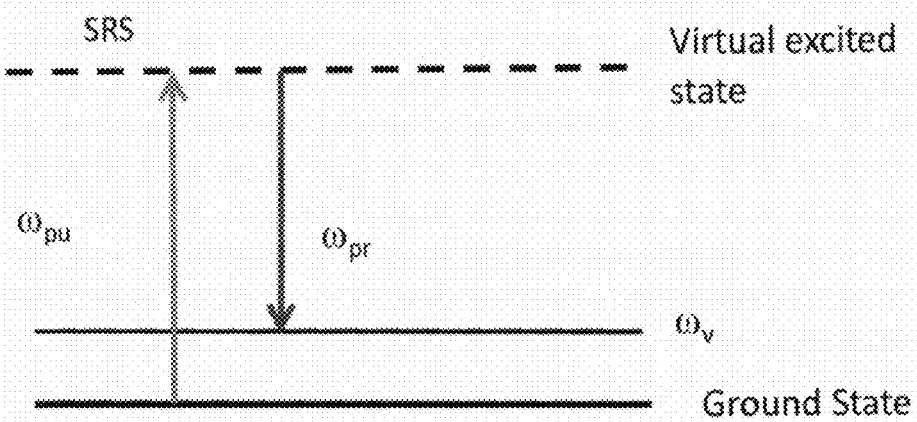
FIG. 10 is an energy level diagram for a stimulated Raman vibrational transition.

The energetics of SRSM is shown in FIG. 10. SRS differs from stimulated fluorescence in that the excited state is a virtual level, with a sub-femtosecond lifetime. Therefore, the pump and probe are delivered simultaneously to the focal region. SRS is a fully coherent process as compared to stimulated fluorescence which is a partially incoherent and partially coherent process. In order to perform the coherent SRS process the pump and probe beams can have the same polarization direction. This is accomplished if the pump and probe beams are linearly polarized along the x axis, which is the one axis transverse to both beamlines.

OC-SRSM (OC-SRSM) uses single photons for excitation and one for stimulated emission. OC-SRSM uses the same setup as stimulated fluorescence shown in FIG. 2.

The use of high speed Raman detection can be used for 3-Dimensional image reconstruction in pathology using CH2 and CH3 vibrational signals to look at nucleic acid and protein signals. Single photon STEM or MP-STEM can be used for 3-Dimensional reconstruction in melanoma or with protein and nucleic acid stimulated fluorescence.

The foregoing Detailed Description is to be understood as being in every respect illustrative, but not restrictive, and the scope of the disclosed technology disclosed herein is not to be determined from the Detailed Description, but rather from the claims as interpreted according to the full breadth permitted by the patent laws. It is to be understood that the implementations shown and described herein are only illustrative of the principles of the disclosed technology and that various modifications can be implemented without departing from the scope and spirit of the disclosed technology.

The invention claimed is:

1. A microscopy system comprising:
a first laser emitting a first laser pulse along a first beam line, the first laser pulse being a Gaussian pump beam; and
a second laser emitting a second laser pulse along a second beam line, the second laser pulse being a probe beam, the Gaussian pump beam and the probe beam arriving at a sample at right angles to each other thereby allowing the Gaussian pump beam to shrink a focal axial diameter of the second beam line and enabling dipole-like backscatter stimulated emission along the second beam line.

2. The microscopy system of claim 1 wherein the Gaussian pump beam and the probe beam remain confocal and are phased to scan across the sample.

3. The microscopy system of claim 1 further comprising: a first objective having a numerical aperture greater than 1, the first objective being positioned along the first beam line; and a second objective having a numerical aperture less than the first objective, the second objective being positioned along the second beam line, wherein the second objective produces an axial focal spot diameter less than 50% of a wavelength of a stimulated emission photon.

4. The microscopy system of claim 1 wherein the Gaussian pump beam is focused to a spot in a sample.

5. The microscopy system of claim 1 wherein the second beamline collects the dipole-like backscattered stimulated emission and focuses the dipole-like backscattered stimulated emission on a confocal aperture array.

6. The microscopy system of claim 1 further comprising: at least one time delay component along the second beam line for delaying the probe beam, the at least one time delay component delaying the probe beam by 0.001 ps to 5 ns relative to the pump beam.

7. The microscopy system of claim 1 wherein the probe beam includes a Gaussian spot at focus.

8. The microscopy system of claim 1 further comprising: a galvanometer scanning system along the first beam line that scans the Gaussian pump beam to fill in a two dimensional image in a detector located along the second beam line.

9. The microscopy system of claim 1 further comprising: a galvanometer scanning system along the second beam line that scans the probe beam to fill in focal spots of the Gaussian pump beam.

10. The microscopy system of claim 1 wherein the microscopy system enables reduction of an axial stimulated emission region half width dimension of a stimulated emission focal spot to less than 50% of a wavelength of a stimulated emission photon.

11. The microscopy system of claim 1 further comprising: an acousto-optic modulator for modulating the Gaussian pump beam on and off.

12. A microscopy method comprising the steps of:
emitting a first laser pulse along a first beam line, the first laser pulse being a Gaussian pump beam;
emitting a second laser pulse along a second beam line, the second laser pulse being a probe beam; and
delivering the Gaussian pump beam and the probe beam to a sample so that the Gaussian pump beam and the probe beam arrive at the sample at right angles to each other thereby allowing the Gaussian pump beam to shrink a focal axial diameter of the second beam line and enabling dipole-like backscatter stimulated emission along the second beam line.

13. The microscopy method of claim 12 wherein the Gaussian pump beam and the probe beam remain confocal and are phased to scan across the sample.

14. The microscopy method of claim 12 wherein a first objective is positioned along the first beam line and has a numerical aperture greater than 1, and a second objective being positioned along the second beam line and has a numerical aperture less than the first objective, the second objective producing an axial focal spot diameter less than 50% of a wavelength of a stimulated emission photon.

15. The microscopy method of claim 12 wherein the Gaussian pump beam is focused to a spot in a sample.

16. The microscopy method of claim 12 wherein the second beamline collects the dipole-like backscattered stimulated emission and focuses the dipole-like backscattered stimulated emission on a confocal aperture array.

17. The microscopy method of claim 12 further comprising the step of: delaying the probe beam by 0.001 ps to 5 ns relative to the pump beam.

18. The microscopy method of claim 12 wherein the probe beam includes a Gaussian spot at focus.

19. The microscopy method of claim 12 further comprising the step of: scanning the Gaussian pump beam along the first beam line to fill in a two dimensional image in a detector located along the second beam line.

20. The microscopy method of claim 12 further comprising the step of: scanning the probe beam along the second beam to fill in focal spots of the Gaussian pump beam.

21. The microscopy method of claim 12 wherein the microscopy system enables reduction of an axial dimension of a stimulated emission focal spot to less than 50% of a wavelength of a stimulated emission photon.

22. The microscopy method of claim 12 further comprising the steps of: modulating the Gaussian pump beam on and off.

* * * * *